(12) United States Patent
Schmiechen

(10) Patent No.: US 11,642,491 B2
(45) Date of Patent: May 9, 2023

(54) APPARATUS FOR VIBRATION CANCELLATION

(71) Applicant: Theodore H. Schmiechen, Philadelphia, PA (US)

(72) Inventor: Theodore H. Schmiechen, Philadelphia, PA (US)

(*) Notice: Subject to any disclaimer, the term of this patent is extended or adjusted under 35 U.S.C. 154(b) by 342 days.

(21) Appl. No.: 16/949,605

(22) Filed: Nov. 6, 2020

(65) Prior Publication Data
US 2021/0170139 A1 Jun. 10, 2021

Related U.S. Application Data

(60) Provisional application No. 62/944,046, filed on Dec. 5, 2019.

(51) Int. Cl.
| | | |
|---|---|---|
| *A61M 21/02* | (2006.01) | |
| *F04D 29/58* | (2006.01) | |
| *F04D 29/40* | (2006.01) | |
| *A61M 21/00* | (2006.01) | |

(52) U.S. Cl.
CPC ........... *A61M 21/02* (2013.01); *F04D 29/403* (2013.01); *F04D 29/582* (2013.01); *A61M 2021/0027* (2013.01); *A61M 2205/362* (2013.01); *A61M 2205/3606* (2013.01); *A61M 2205/502* (2013.01); *A61M 2205/587* (2013.01); *A61M 2205/8206* (2013.01)

(58) Field of Classification Search
CPC .......... A61M 21/02; A61M 2021/0027; A61M 2205/3606; A61M 2205/362; A61M 2205/502; A61M 2205/587; A61M 2205/8206; F04D 29/403; F04D 29/582; G10K 11/1752; B06B 1/10
USPC ..................................................... 600/26–28
See application file for complete search history.

(56) References Cited

U.S. PATENT DOCUMENTS

| | | | | |
|---|---|---|---|---|
| 4,133,305 | A * | 1/1979 | Steuer .................. | A47C 21/006 5/915 |
| 5,007,410 | A * | 4/1991 | DeLaney ........... | A61H 23/0263 5/915 |
| 2005/0277856 | A1* | 12/2005 | Munro .................... | A61H 23/02 601/57 |
| 2007/0239088 | A1* | 10/2007 | Wu ......................... | A61H 1/005 601/30 |
| 2009/0127020 | A1* | 5/2009 | Connor ............... | G10K 11/1752 181/141 |
| 2010/0268121 | A1* | 10/2010 | Kilborn ................. | A61B 5/412 600/587 |
| 2012/0016274 | A1* | 1/2012 | Howe .................... | A61M 21/02 601/148 |
| 2014/0013515 | A1* | 1/2014 | Richards ................. | G16Z 99/00 5/715 |
| 2015/0320588 | A1* | 11/2015 | Connor ................. | A61F 7/0085 607/104 |
| 2016/0066716 | A1* | 3/2016 | Rao ...................... | A61B 5/6814 600/26 |

(Continued)

*Primary Examiner* — Sunita Reddy

(57) ABSTRACT

A method, system and apparatus for a vibration-masking device for use in the bed emits sufficient vibration to mask ambient vibrations and aid in sleep and relaxation. Low frequency vibrations also help reduce the risk of deep vein thrombosis, also referred to as DVT. The apparatus is designed to be cooled so as to avoid overheating when used in the bed or in upholstered furniture.

2 Claims, 9 Drawing Sheets

(56) References Cited

U.S. PATENT DOCUMENTS

| | | | |
|---|---|---|---|
| 2016/0144151 A1* | 5/2016 | McNew | A61M 21/02 |
| | | | 600/28 |
| 2016/0199241 A1* | 7/2016 | Rapoport | G10K 11/162 |
| | | | 600/22 |
| 2017/0053637 A1* | 2/2017 | DeFranks | G10K 11/17817 |
| 2018/0110960 A1* | 4/2018 | Youngblood | A47C 21/048 |
| 2019/0320808 A1* | 10/2019 | Chapin | A47C 21/044 |
| 2020/0246579 A1* | 8/2020 | Cohen | A61H 1/003 |
| 2020/0337470 A1* | 10/2020 | Sayadi | A47C 31/123 |
| 2022/0152340 A1* | 5/2022 | de Goeij | A61M 21/02 |

* cited by examiner

300

APPARATUS FOR VIBRATION CANCELLATION

TECHNICAL FIELD

The present disclosure relates to vibrating devices and specifically to devices that provide noise masking by the use of vibration.

BACKGROUND

Noise-masking devices for proper sleep and relaxation usually generate opposing noise to mask sound. Sound-producing machines and computer applications produce white, pink, brown and other "colors" of noise that mask sound by emitting constant, random sound across all frequencies audible to the human ear. Pink noise has reduced, higher frequencies than white noise; brown noise has comparatively lower frequencies.

Sound and vibration are closely related. Sound occurs in pressure waves, which are generated by vibrating structures (for example vocal chords). These pressure waves can induce the vibration of structures (such as the ear drum). Similar to noise-generators, vibrating devices are designed to reduce noise by producing vibrations instead of sounds. Common vibrating devices are designed for use in household furniture, especially bedding, to produce constant, low-frequency vibrations meant to mask ambient vibrations and soothe a person to sleep.

A wavelength of a vibration is defined as the distance from one wave peak to the next. The maximum height of a wave is referred to as amplitude or power. The amount of waves over a given length of time is referred to as frequency. The term Hertz is a measurement of wave-cycles per second. The audible range of vibration in Hertz is between 20 Hz and 20,000 Hz. Mechanical or seismic vibrations can be felt in ranges below 20 Hz.

Forceful changes in sound occur in a higher amplitude (power) than the common range of frequencies in white noise. Forceful changes in sound may be best masked by vibrations with similar amplitudes to those of the unwanted sound. Because of its relatively greater amplitude, physical vibration is more likely to mask forceful changes than audible vibration. As audible vibration masks audible changes in sound, physical vibration masks harsh changes in sound that are accompanied by a sound wave that can be felt physically.

Sound waves with a frequency below the lower limit of audibility (20 Hz) is referred to as low-frequency sound or infrasound. Although 20 Hz is considered the lower limit of human hearing, humans can perceive sound in frequencies lower than 20 Hz if the intensity of sound is high enough. It is known in the art that vibration at a fixed frequency can mask noise and have a soothing effect; vibration therapy is used to treat restless-leg syndrome, peripheral neuropathic pain and phantom-nerve impulses. These low frequency vibrations also help reduce the risk of deep vein thrombosis, also referred to as DVT, particularly in the lower legs and during post-surgery recovery.

It is commonly known that light influences human circadian rhythms, and that stimuli from modern technologies can disturb these rhythms and affect sleep. Electronic-device screens expose humans to relatively intense sources of blue and green light. Light-emitting diodes (LED) that emit blue or green light can disrupt sleep. Household appliances often use lighted switches that cause unwanted light in bedrooms at night.

A bimetal switch uses a bimetal strip to convert a temperature change into a mechanical displacement which is in turn used to trip a switch. A bimetal strip has two strips of differing metals (usually steel and copper) which expand at differing rates as they are heated. When heated, the strip bends toward the side having the metal of lower coefficient of thermal expansion. A bimetal switch uses the bending motion of a bimetal strip to open or close a switch. A heat-sensitive switch on a motor opens a switch at a given temperature beyond which damage may occur to the motor.

Pulse-width modulation (PWM) is a method of reducing the average power delivered by an electrical source by effectively breaking the electrical signal into discrete parts. The average value of voltage and current transferred to a load is controlled by turning the switch between the supply and the load on and off at a rapid rate. A PWM is commonly used to control the speed of a motor. By controlling the amount of power delivered to a motor, speed can vary without the losses that would result from linear power delivered by resistive means. Losses associated with resistive means result in excessive heat in the motor. Controlling motor speed by PWM is a method of controlling speed without excessive heat buildup in the motor.

Low-intensity vibrator motors are intended for long-term use. High-intensity motors are for short-term use. Long-term use of high-intensity, motor-driven vibrators can result in excessive heat or combustion. A cooling fan may be used to dissipate this heat. However in household applications, vibration devices that are intended for use with bedding or upholstery would pose a fire hazard.

SUMMARY

A method, system and apparatus for a vibration-masking device for use in the bed has a motor-driven vibrator contained in a cooled housing, and a control unit contained in a tethered cooled housing. In an example embodiment, a motorized vibrator housing is tethered by wiring harness to a control unit. The control unit houses a fan and a pulse-width modulator (PWM) which is controlled by an external knob. The fan pulls air through the vent, past the PWM and out of the housing. The control unit has a reverse-illuminated switch, with its light going off at activation and on at deactivation. A motor/vibrator is contained in a cooled housing, which has a fan that pulls air through a vent, past the motorized vibrator and out of the housing. The motorized vibrator housing has a magnetic surface that mates with a ferrous plate designed to be placed under household bedsheets. The ferrous plate may be made of steel, iron, magnetic stainless steel, or of any number of magnetic polymers. The ferrous plate may be placed under bedclothes or beneath a mattress pad. The housing joins magnetically through the bedding to hold the housing in place near the user. The placement of the apparatus with a magnetic plate beneath bedding allows the unit to be moved to a specific location. For example, a user may move the apparatus close to a limb that is experiencing sleep-disrupting nerve impulses.

PWM is varied by a potentiometer and controls the amount of power and thus the speed of the motor. Greater motor speed produces higher-frequency vibrations; lower motor speed delivers lower-frequency vibrations. The use of PWM results in less heat generation than linear-power control methods, which rely on resistance to vary the power.

In another embodiment the motorized vibrator housing is tethered to the control unit by a conduit that is coaxial with the cables that power the motor. The conduit terminates at the control unit, which has an exhaust fan for pulling air through the conduit and out into the environment. Air is drawn through a vent in the motorized vibrator housing, past the motor, through the conduit, and past the PWM electronics to the exhaust fan in the control unit. From there it is expelled into the environment. One fan keeps both the motor and the power electronics cool and continues to provide airflow should the unit become covered by bedclothes.

In a third iteration of the embodiment, a motorized vibrator housing is tethered to a control unit housing by a combination fluid and electrical conduit. A control-unit housing has a reverse-illuminated switch, a timer, a PWM, a vent, a fan and a fluid pump. The reverse-illuminated switch has an LED that is lit when the unit is off and is dark when the unit is on. The timer shuts the unit off after a set period of time. The PWM in combination with the motorized vibrator controls the frequency of the motorized vibrator vibrations. In some embodiments, the motorized vibrator produces vibrations of a frequency between 1 Hz and 30 Hz. The fan moves air through the vent and out of the control-unit housing. The fluid pump is connected to the combination fluid and electrical conduit and further coupled with the motorized vibrator so as to pull air from the vicinity of the motorized vibrator through the conduit and out through the vent. By pulling air with the pump, the motorized vibrator is kept cool in the event that it is covered by bedding. In one method of use, the apparatus is covered with a towel and placed between the user's legs for the purpose of DVT-related blood clot prevention. One skilled in the art understands that ordinary vented motors of the state-of-the-art would overheat in such a situation.

In any embodiment, a bimetal switch in the circuit may be placed against the motor to break the circuit if the motor exceeds a heat threshold. The control unit apparatus is intended for use proximal to a bed and includes an LED-illuminated switch that is lit when the unit is off and is dark when the unit is on. A switch that is illuminated in the "off" position and dark in the "on" position is better suited to a sleep environment.

The following drawings are designed to illustrate rather than define the limits of the invention.

DESCRIPTION

Figure 1:
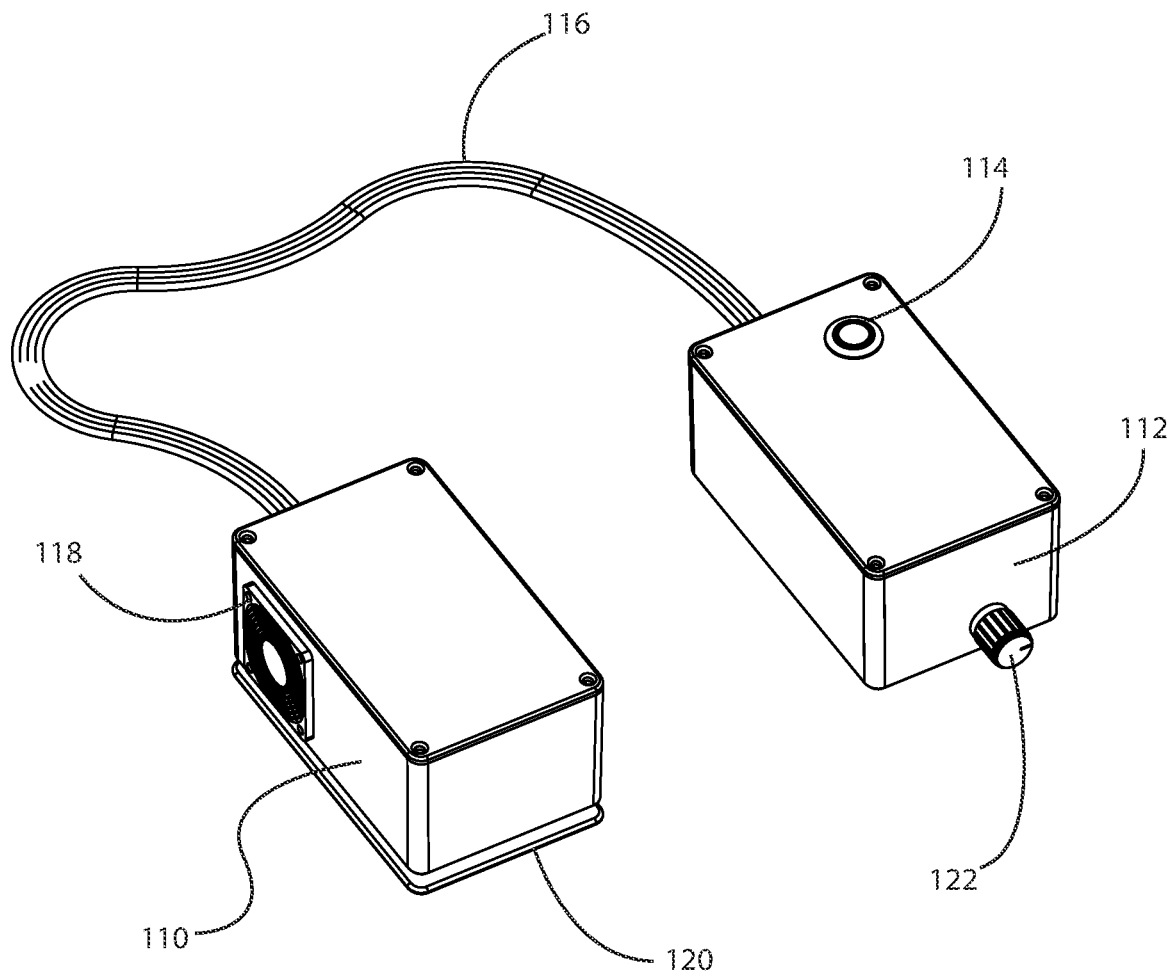
FIG. 1 is a perspective view of the embodiment 100.

The present disclosure relates to a vibrator-and-control assembly 100 (FIG. 1) intended for use in a bed. A motorized vibrator housing 110 is tethered by wiring harness 116 to a control unit 112. The motor housing is 110 magnetically joined to a ferrous plate 120. The housing has a vent fan 118 for cooling the motor. The control unit 112 has a light-emitting diode (LED) switch 114. In the "off" position the switch 114 is illuminated; in the "on" position the light is off. A control knob 122 controls a pulse-width modulator 130 (FIG. 2).

Figure 2:
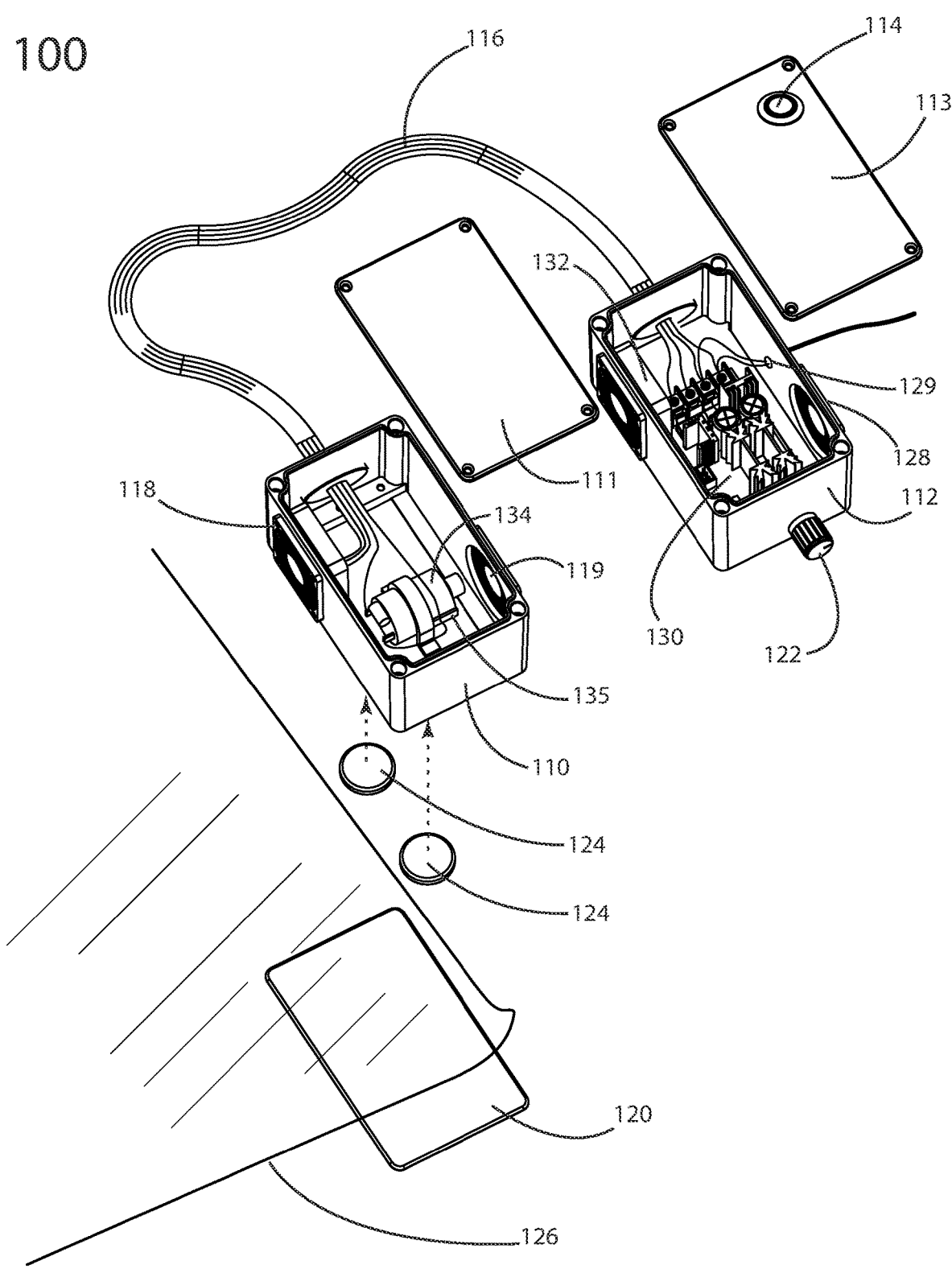
FIG. 2 is a partially exploded perspective view thereof.

FIG. 2 is a partially exploded view of the embodiment of FIG. 1. Power is supplied to the unit by a 12V power source 129. The motorized vibrator 134 is mounted to the motorized vibrator housing 110. Wires from the wiring harness 116 power the motorized vibrator 134 and fan 118. A bimetal coupling 135 is part of the circuit that powers the motorized vibrator to prevent overheating of the motorized vibrator. The fan 118 pulls air through a vent 119 to dissipate heat in the housing 110. A cover 111 encloses the housing 110. Magnets 124 are affixed to the underside of the motorized vibrator housing 110 and mate with a ferrous plate 120 that is designed to be placed under bedclothes 126. One skilled in the art understands that bedclothes 126 may be any thickness or number of layers of sheets, blankets, mattress pads and the like.

The wiring harness 116 joins the motorized vibrator housing to the control unit 112. Power is supplied to the system by a 12V source 129. One skilled in the art understands that the unit may also be powered by on-board batteries. The control unit 112 houses a fan 132 and a PWM 130 which is controlled by control knob 122. The fan pulls air through the vent 128, past the PWM and out via fan 132.

A cover 113 encloses the control unit 112 and supports the reverse-illuminated switch 114. The switch 114 is illuminated with an internal light emitting diode (LED) in the "off" position and is turned off when the switch is in the "on" position so as to preserve darkness during operation in a room at night.

Figure 3:
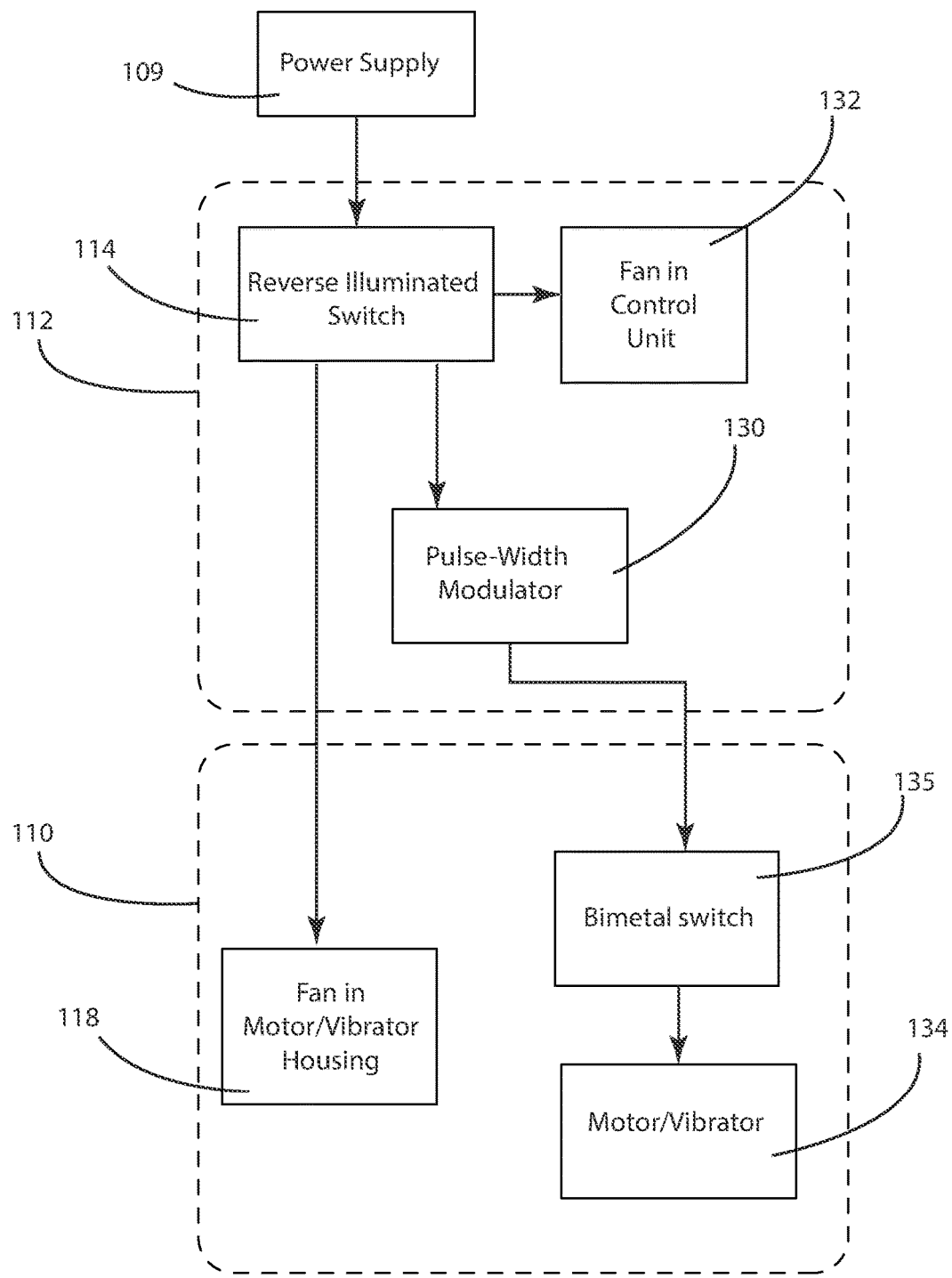
FIG. 3 is a diagram thereof.

FIG. 3 100 is a diagram of the apparatus of FIG. 1 and FIG. 2. Dashed lines represent the control unit 112 and the motorized vibrator housing 110 as well as the components contained therein. A power supply 109 is controlled by the reverse-illuminated switch 114. Power is directed to the fan 132 in the control unit 112 as well as to the fan in the motorized vibrator housing 118. Power is also directed to the PWM 130 and through the bimetal switch 135 to the motorized vibrator 134.

Figure 4:
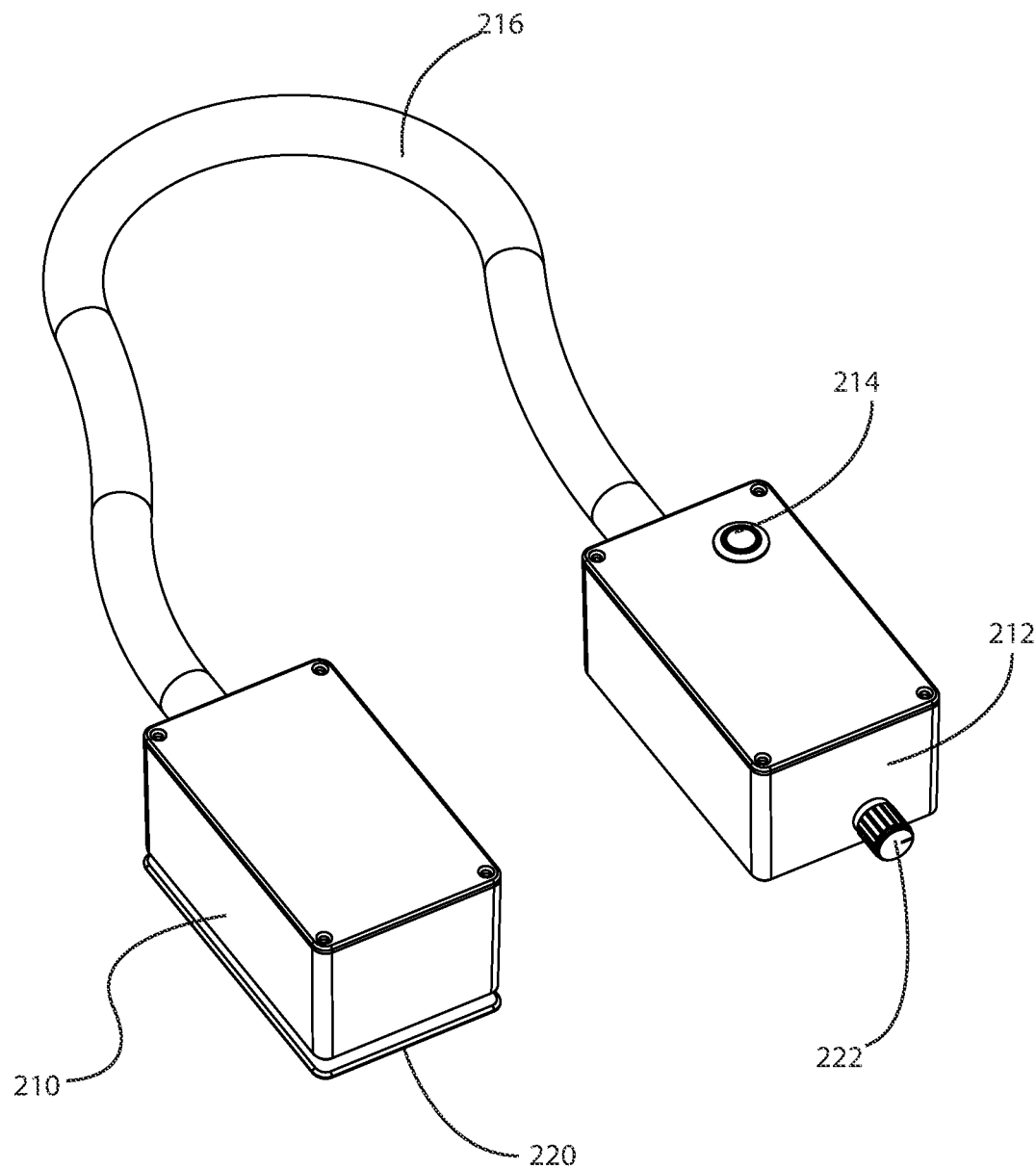
FIG. 4 is a perspective view of an iteration 200 of the embodiment.

FIG. 4 depicts another iteration 200 of the embodiment. A motorized vibrator housing 210 houses a motorized vibrator and is magnetically joined to a ferrous plate 220. The motorized vibrator housing is tethered by a conduit with coaxial wires 216 to a control unit 212. The control unit 212 has a reverse-illuminated switch 214. The switch 214 is illuminated with an internal light emitting diode (LED) in the "off" position and is dark when the switch is in the "on" position.

Figure 5:
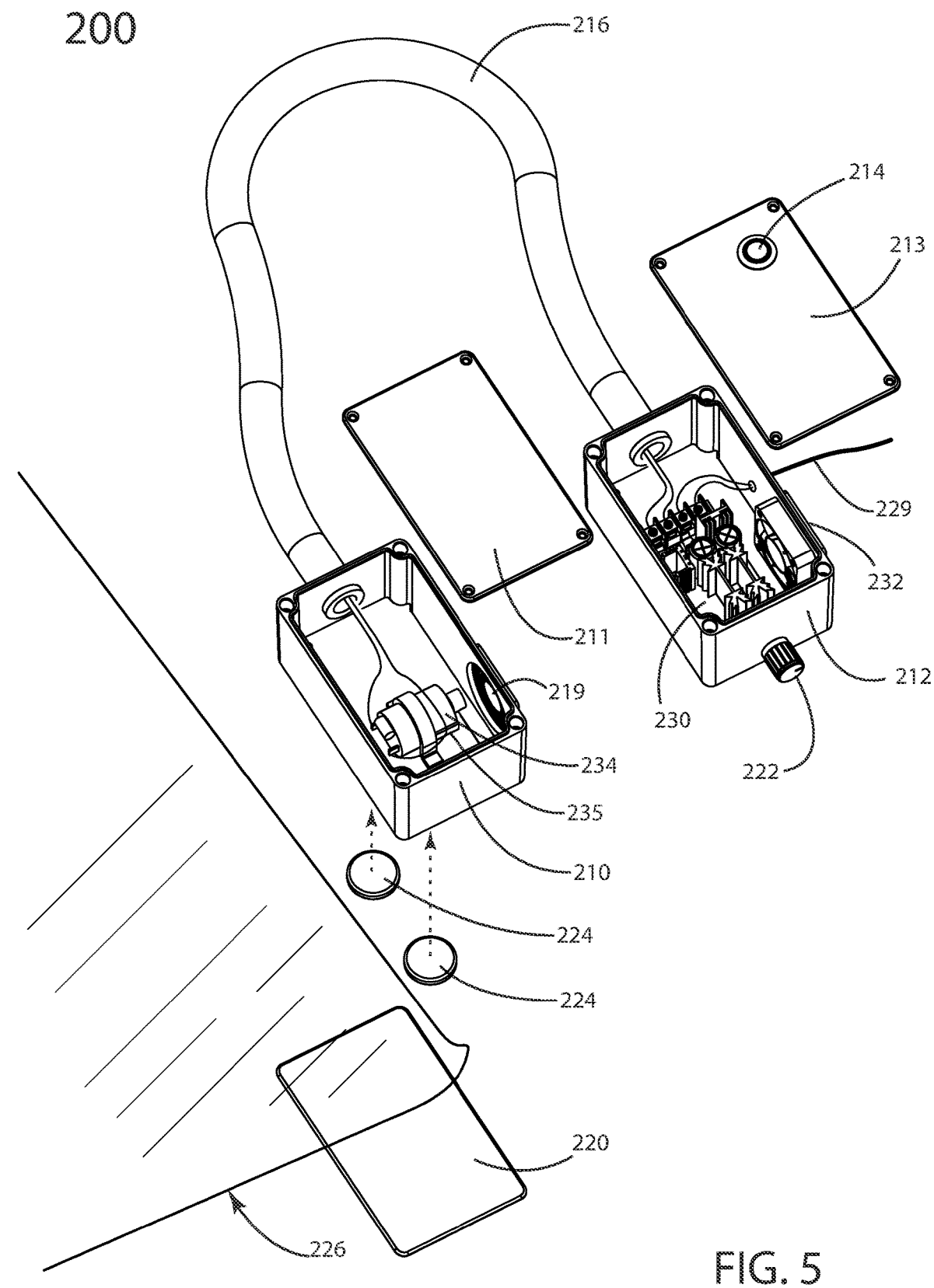
FIG. 5 is a partially exploded perspective view thereof.

FIG. 5 is a partially exploded view of the embodiment of FIG. 4. Power is supplied to the unit by a 12V power source 229. The motorized vibrator 234 is mounted to the motorized vibrator housing 210. The control unit 212 houses a fan 232 and a PWM 230 which is controlled by control knob 222. Coaxial wires in a conduit 216 power the motorized vibrator. A bimetal coupling 235 is part of the circuit that powers the motorized vibrator to prevent overheating of the motorized vibrator. The fan 232 pulls air from vent 219 past the motorized vibrator 234, through the conduit 216, past the PWM 230, to dissipate heat in the housing 210 and the control unit 212. A cover 211 encloses the housing 210 and a cover 213 encloses the control unit 212. The control unit 212 has a reverse-illuminated switch 214. Magnets 224 are affixed to the underside of the motorized vibrator housing 210 and mate with a ferrous plate 220 that is placed under bedclothes 226. One skilled in the art understands that bedclothes 226 may be any thickness or number of layers and may include sheets, blankets, mattress pads and the like.

Figure 6:
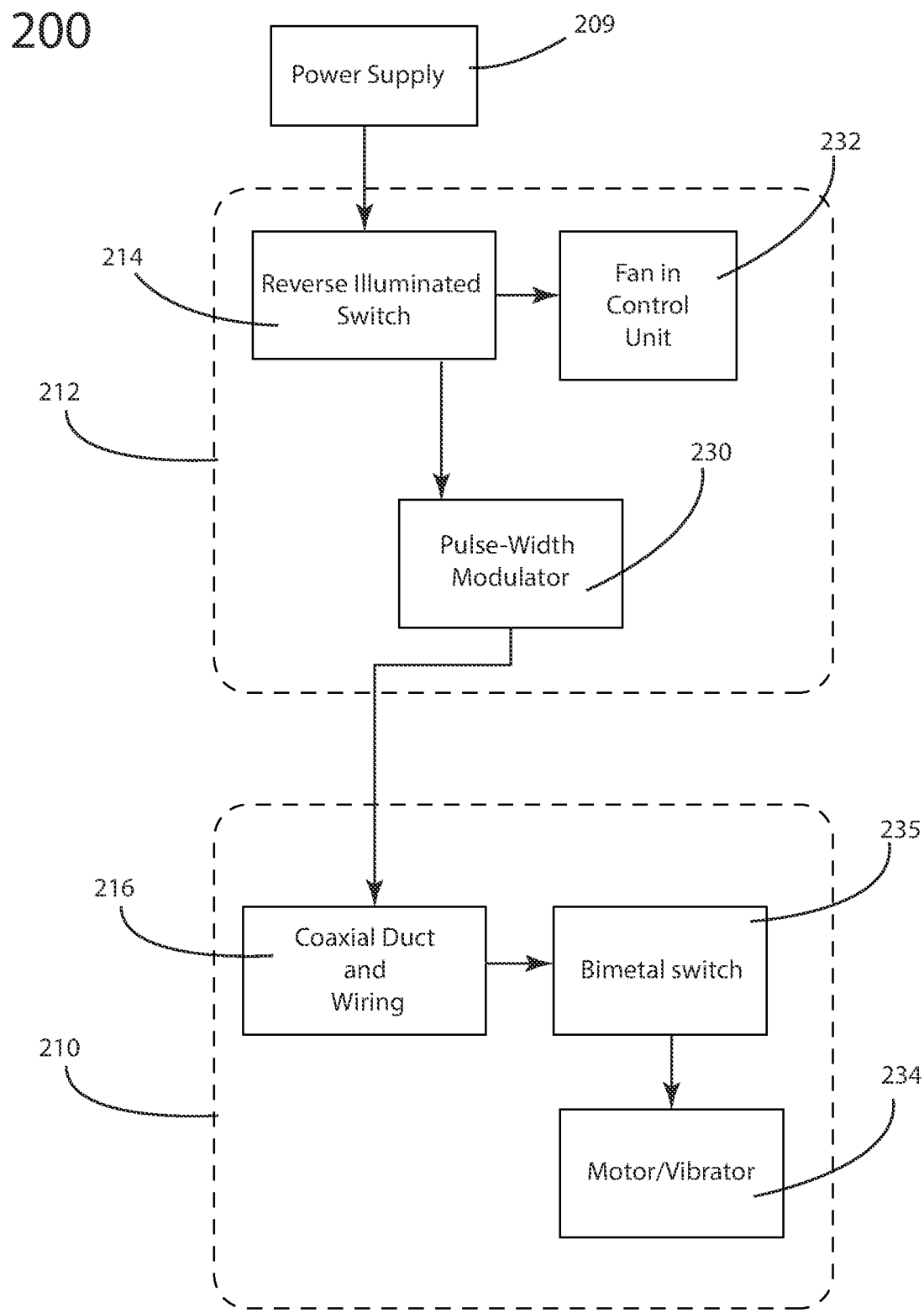
FIG. 6 is a diagram thereof.

FIG. 6, 200 is a diagram of the apparatus of FIG. 4 and FIG. 5. Dashed lines represent the control unit 212 and the motorized vibrator housing 210 as well as the components contained therein. A power supply 209 is controlled by the reverse-illuminated switch 214. Power is directed to the fan 232 in the control unit 212. Power is also directed to the PWM 230 and through the coaxial duct and wiring 216 to the bimetal switch 235 and to the motorized vibrator 234.

Figure 7:
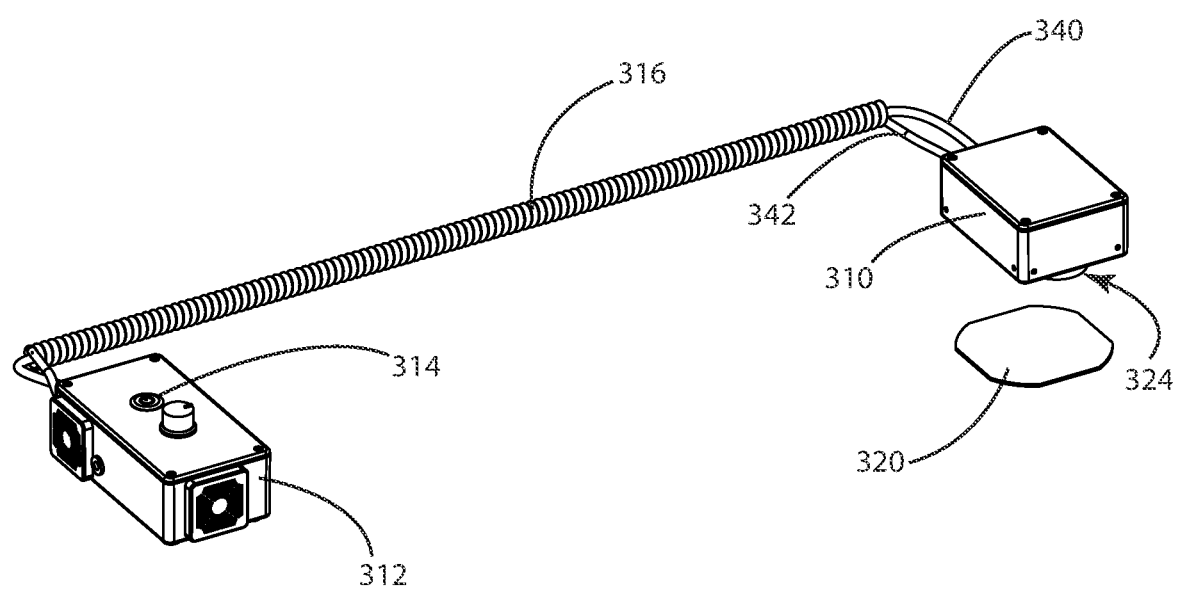
FIG. 7 is a perspective view of an iteration 300 of the embodiment.

FIG. 7 depicts another iteration 300 of the embodiment. A motorized vibrator housing 310 is joined by magnets 324 to a ferrous plate 320. The motorized vibrator housing is tethered by a conduit 316 with coaxial wires to a control unit 312. The conduit 316 is made up of tubing 340 and wiring 342. The control unit 312 has a reverse-illuminated switch 314. The switch 314 is illuminated with an internal light emitting diode (LED) in the "off" position and is dark when the switch is in the "on" position. One skilled in the art understands that a housing such as motorized vibrator housing 310 may include any number of holes for ventilation and that such holes may be in any of the side walls, top or bottom surfaces of the housing.

Figure 8:
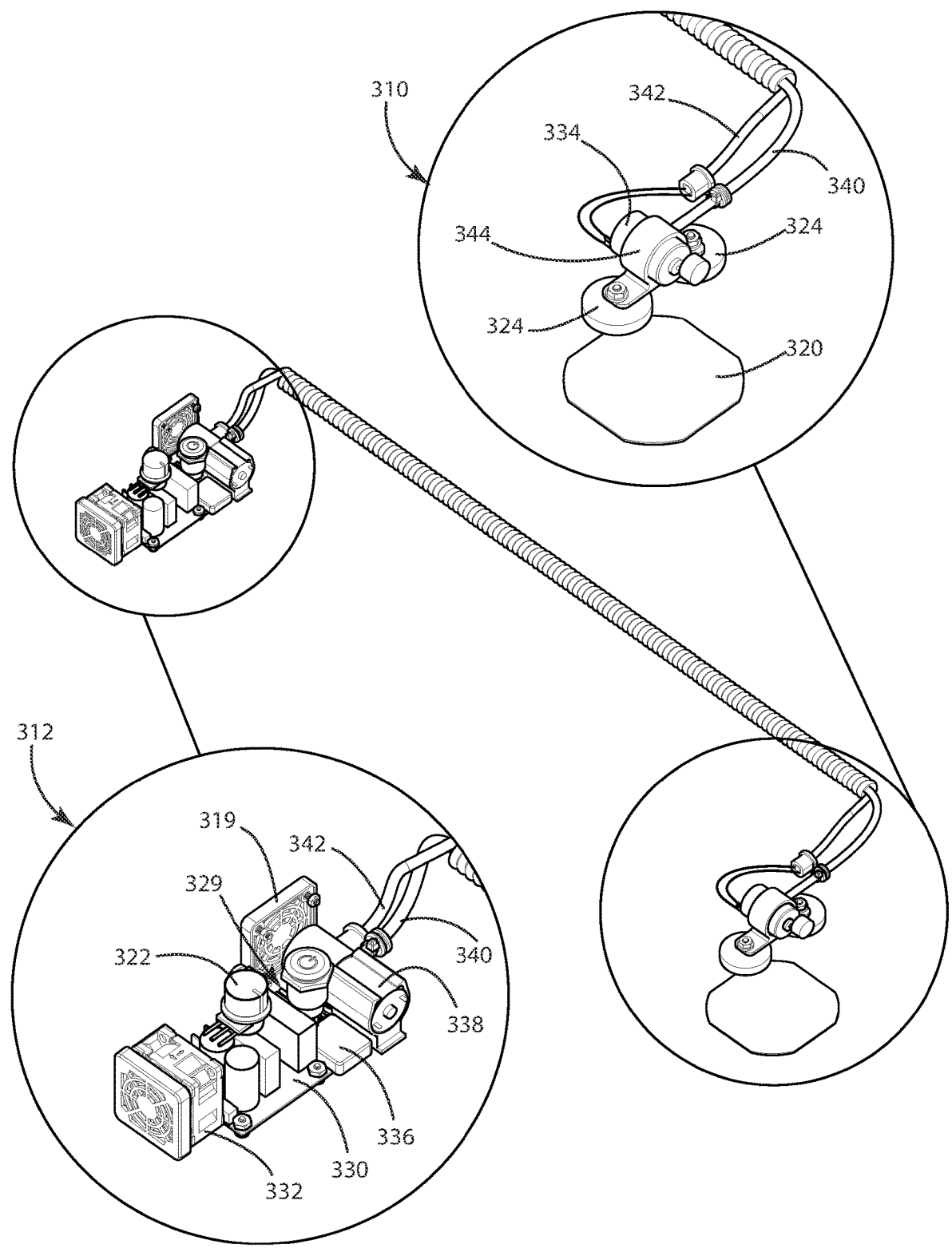
FIG. 8 is a partially exploded perspective view thereof, with housings removed.

FIG. 8 is a partially exploded view of the embodiment of FIG. 7. In some embodiments a power source 329 is a 12V power source. The motorized vibrator 334 is mounted to the motorized vibrator housing 310. The control unit 312 houses a fan 332 and a PWM 330 which is controlled by control knob 322. Coaxial wires 342 and tubing 340, combined coaxially 316, serve to power and cool the motorized vibrator. The motorized vibrator produces vibration in frequencies between 1 Hz and 30 Hz. Heat generated by the motorized vibrator can accumulate in the control-unit housing 312; this heat is dispelled by the fan 332 which pulls air from vent 319 past the PWM 330. A pump 338 pulls air through tubing 340 that is in turn connected to a vented motor housing 344 such that air is pulled past the motorized vibrator 334 to keep it cool. One skilled in the art understands that pulling the air with a pump through a conduit ensures the flow of air over the motorized vibrator in the event that the motorized vibrator housing becomes covered with bedclothes. The control unit 312 has a reverse-illuminated switch 314. Magnets 324 are affixed to the underside of the motorized vibrator housing 310 and mate with a ferrous plate 320 that is placed under bedclothes. The PWM 330 controls the pump 338. One skilled in the art understands that running the pump 338 relatively slower when the motorized vibrator 334 is running relatively slower, energy usage and noise are kept at a minimum.

Figure 9:
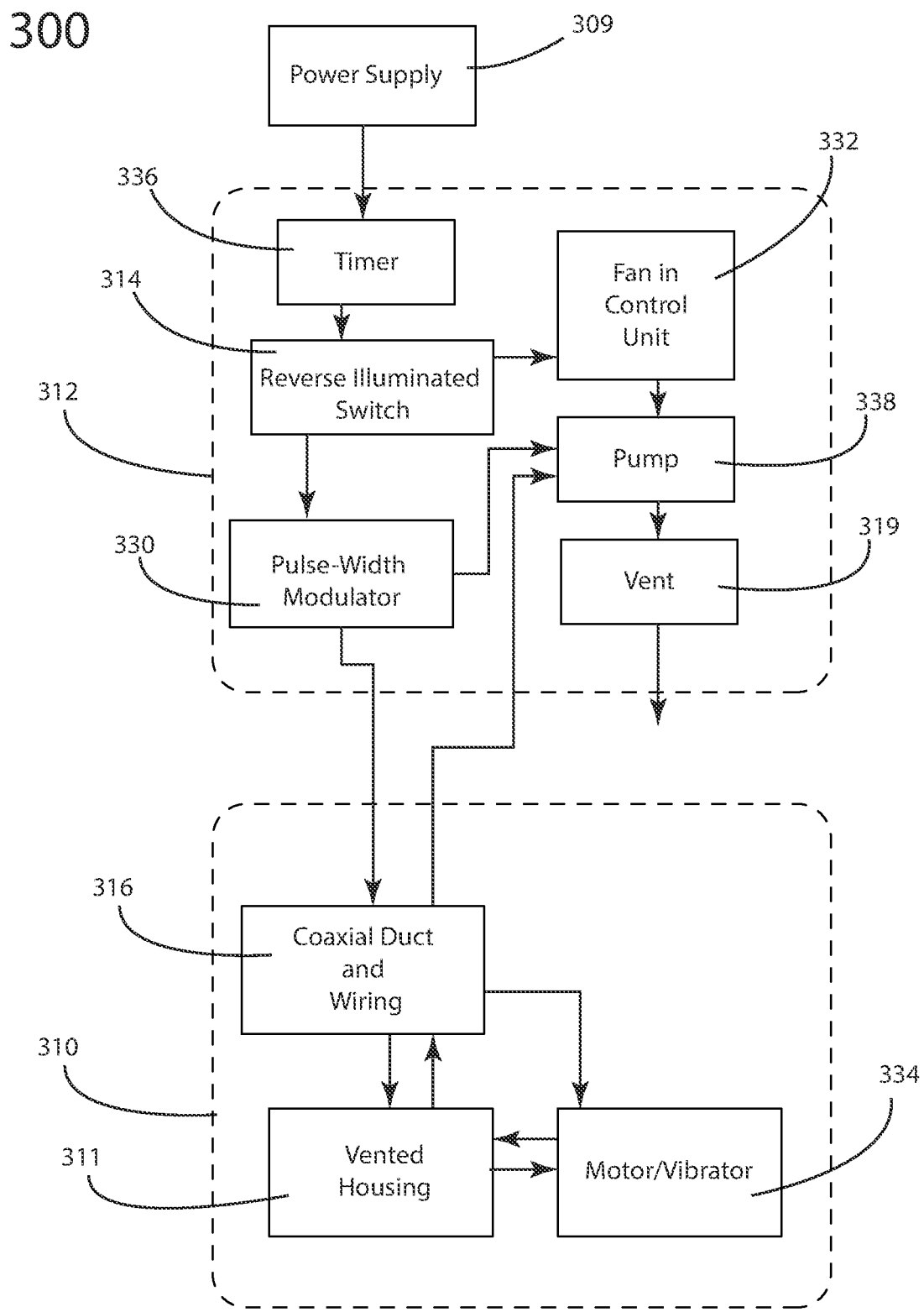
FIG. 9 is a diagram thereof.

FIG. 9 is a diagram of the apparatus 300 of FIGS. 7 and 8. Dashed lines represent the control unit 312 and the motorized vibrator housing 310 and the components contained therein. A power supply 309 is controlled by a timer 336 that shuts the power off after a set time to prevent overheating. In some embodiments the timer 336 shuts the power off after ten hours of continuous use. The power continues from the timer to the reverse-illuminated switch 314. Power is directed to the fan 332 in the control unit 312 and to a pulse-width modulator 330. The pulse-width modulator powers and controls a fluid pump 338 as well as a motor/vibrator 334, also referred to as a motorized vibrator 334. A vent 319 allows expelled air from the pump 338 to flow out of the housing 312. The pump pulls air from the area surrounding the motorized vibrator 334 so that the motorized vibrator 334 is kept cool even if bedding covers the motorized vibrator housing 310. Power directed to the PWM 330 is also directed through the coaxial duct and wiring 316 to the motorized vibrator 334. A duct in the coaxial duct and wiring 316 is in fluid communication with a vented housing 311 that surrounds the motorized vibrator 334. Heat is directed from the motorized vibrator 334 through the vented housing 311, through the coaxial duct and wiring 316 to the pump 338 where it is dispelled through the vent 319.

The motorized vibrator 334, in combination with the pulse-width modulator 330, generates a vibration in the range of 1 Hz to 30 Hz and is capable of generating vibrations of wavelengths below 20 Hz for up to 10 hours continuously.

The invention claimed is:

1. A sleep-aid apparatus for vibrating a ferrous surface placed under bedclothes to aid sleep by masking infrasonic low-frequency ambient noise, the apparatus comprising:
   a power supply; and
   a reverse-illuminated switch electronically coupled with said power supply; and
   a first housing; and
   a second housing; and
   a combination fluid and electrical conduit for fluidly and electronically coupling said first housing with said second housing; and
   a programmable, timed switch fixedly engaged with said first housing and electronically coupled with said reverse-illuminated switch; and
   a fan fixedly engaged within said first housing and electronically coupled with said timed switch configured to move air through said first housing; and
   a pulse-width modulator fixedly engaged within said first housing and electronically coupled with said timed switch; and
   said pulse-width modulator configured to control the motorized vibrator to generate vibrations between 1 Hz and 30 Hz for vibrating the ferrous surface while masking infrasonic low-frequency ambient noise; and
   said pulse-width modulator further electronically coupled through said fluid and electrical conduit with a motorized vibrator; and
   said motorized vibrator fixedly engaged within said second housing; and
   a fluid pump fixedly engaged with said first housing and electronically coupled with said timed switch and electronically coupled with said pulse-width modulator and fluidly coupled with said motorized vibrator; wherein said first housing is kept cool by said fan moving air through said first housing, and said motorized vibrator is kept cool by fluid moved by said pump through said combination fluid and electrical conduit and past said motorized vibrator.

2. The apparatus of claim 1, wherein the pulse-width modulator is configured to control the motorized vibrator to generate vibrations below 20 Hz.

* * * * *